United States Patent [19]

Miwa et al.

[11] 4,434,661
[45] Mar. 6, 1984

[54] ULTRASONIC DIAGNOSTIC SYSTEM

[75] Inventors: Hirohide Miwa, Kawasaki; Takaki Shimura, Machida, both of Japan

[73] Assignee: Fujitsu Limited, Kawasaki, Japan

[21] Appl. No.: 209,403

[22] PCT Filed: Jan. 30, 1980

[86] PCT No.: PCT/JP80/00015
§ 371 Date: Oct. 3, 1980
§ 102(e) Date: Sep. 22, 1980

[87] PCT Pub. No.: WO80/01537
PCT Pub. Date: Aug. 7, 1980

[30] Foreign Application Priority Data

Feb. 3, 1979 [JP] Japan ............... 54-11587

[51] Int. Cl.³ ............................. G01N 29/00
[52] U.S. Cl. ...................... 73/625; 73/626; 73/628; 128/660
[58] Field of Search ............. 73/628, 618, 620, 624, 73/625, 626, 627, 631, 641, 609, 610; 128/660

[56] References Cited

U.S. PATENT DOCUMENTS

| | | | |
|---|---|---|---|
| 3,156,110 | 11/1964 | Clynes | 73/628 |
| 3,690,153 | 9/1972 | Matay | 73/631 |
| 4,119,938 | 10/1978 | Alais | 73/620 |
| 4,206,654 | 6/1980 | Keller et al. | 73/620 |
| 4,209,022 | 6/1980 | Dory | 128/660 |
| 4,318,413 | 3/1982 | Iinuma et al. | 128/660 |

FOREIGN PATENT DOCUMENTS 53-96285  8/1978  Japan .

*Primary Examiner*—Stephen A. Kreitman
*Attorney, Agent, or Firm*—Staas & Halsey

[57] ABSTRACT

An ultrasonic diagnostic system for observing the state within a measured object by transmitting ultrasonic waves to the interior of a measured object such as the human body and by receiving acoustic waves reflected from the object. The system employs plural probe units which contain electric-acoustic transducers and are mutually isolated. A transmitting circuit causes the plural probe units almost simultaneously to transmit ultrasonic waves having different characteristics. A receiving circuit contains filters for isolating and extracting acoustic signals having characteristics corresponding to those particular transmitted ultrasonic waves from the other acoustic signals received. This system thereby obtains an acoustic image corresponding to each scanning line, and by means of scanning the measured object with each of the probe units, a display of the object's movement is obtained with plural scanning lines.

20 Claims, 28 Drawing Figures

SCANNING RANGE

FIG. 14B.

ULTRASONIC DIAGNOSTIC SYSTEM

BACKGROUND OF THE INVENTION

This invention relates to an ultrasonic diagnostic system for observing internal conditions of measured objects by emitting an ultrasonic wave into a measured object, such as a human body and by receiving an acoustic wave based on said ultrasonic wave from inside of the measured object.

An ultrasonic diagnostic system is widely used in order to obtain a tomographic image within a human body. In an ultrasonic diagnostic system, the ultrasonic wave pulse is emitted to the human body, an echo wave, diffracted wave or transmission wave returning from a human body is received and thereby a tomographic image indicating tissue within a human body can be obtained based on the received wave. Namely, such ultrasonic diagnostic system has such a merit of not being invasionable and dangerous, such as an X-ray.

An ultrasonic diagnostic system widely used in general utilizes a pulse echo method of operation. The operation of such an ultrasonic diagnostic system will be explained based on this pulse echo method as an example. The ultrasonic wave pulse of 1 MHz to 10 MHz is emitted to an object from the probe containing the piezoelectric element and converted to an electrical signal. Location information of said mismatching areas can be obtained by displaying the above electrical signal. (This process is called an A-mode). A tomographic image can be obtained by means of sequentially shifting the location or angle of the ultrasonic wave pulse emitting probe in accordance with tomography. Location information of mismatching areas is displayed in accordance with the echo waves of emitted pulses. (This process is called a B-mode.)

In such prior ultrasonic diagnostic systems, the ultrasonic wave pulse emission period is limited to a period which does not elapse until the echo pulse is completely received, since a nest ultrasonic wave pulse is emitted only after a period sufficient for the preceding pulse to return as the echo pulse.

Namely, since a velocity of an ultrasonic wave within a human body is above 1500 m/sec, when a maximum diagnostic depth is considered as L (in meters), the period required for a process from pulse emission to reception of echo is 2L/1500 (sec) and therefor the minimum pulse emission period is 2L/1500 (sec).

Thus, the number of scanning lines obtained in one second is limited to 1500/2L (lines). For example, when L=0.2 m, said number of scanning lines becomes 3750, and it is impossible to obtain sufficient scanning lines in such a case where a tomographic image is required within a very short period of time (0.1 sec) for example.

This restriction on the scanning lines results in a problem when displaying a tomographic image on an ordinary CRT display unit.

Namely, since a frame speed of about 30 frames/sec is necessary for display of movement within a human body without the display flickering. For an ultrasonic device in this application, the number of, the scanning lines of one frame is limited to 25 lines/L, while in a television receiver, when L32 0.2 m, there are 512 scanning lines per frame. This means that a tomographic image is displayed very roughly as compared with the television image, thus curtailing a diagnostic effect.

In other words, the prior ultrasonic diagnostic system cannot obtain the sufficient number of scanning lines for displaying the changes of a dynamic organ such as the heart due to the intrinsic limitation of sound velocity. Consequently the tomographic image of the momentary state of the dynamic organ is displayed very roughly. Thus, the elimination of this disadvantage is especially desired.

The number of scanning lines can be increased very easily by preparing a plurality of probes containing piezoelectric elements and emitting the ultrasonic waves from these probes simultaneously. Such technology is already disclosed in the Japanese published patent application No. 53-96285. However, when the ultrasonic waves of the same frequency are emitted simultaneously from a plurality of probes, it is impossible to distinguish the echo pulses of one probe from the echo pulses of the other probes at the time of reception.

Such a known ultrasonic diagnostic system has a problem that the acoustic waves interfere mutually due to the ultrasonic waves being emitted simultaneously. Thus, in actual operation only an image containing a certain degree of noise can be obtained. Another problem is that a combined display on the screen is difficult to obtain because location detection of the probes is not carried out.

SUMMARY OF THE INVENTION

It is an object of this invention to offer an ultrasonic diagnostic system which assures internal image of the measured object without any interference even when ultrasonic waves are emitted simultaneously in order to increase the number of scanning lines.

It is another object of this invention to offer an ultrasonic diagnostic system which assures that the image obtained by emission of ultrasonic waves from a plurality of probes can be combined with excellent accuracy.

In order to attain this objective, this invention is characterized as follows. The ultrsasonic waves having different characteristics (for example, different frequencies) are emitted almost simultaneously from a plurality of probes containing electric-acoustic transducers thereby providing plural scanning lines; the acoustic waves corresponding to these ultrasonic waves are received by the probe units and converted to electrical signals reflecting the characteristics of the acoustic waves; and an electrical signal corresponding to a particular emitted ultrasonic wave is extracted by a filter from the other electrical signals, and thus an image containing internal information can be obtained without distortion from the interferences between simultaneously emitted ultrasonic waves.

Further, this invention assures highly accurate combination of internal image information irrespective of locations of the plural probe units. This is done by mechanically coupling plural probe units and detecting secondary dimensional locations of the coupled plural probes.

DESCRIPTION OF THE PREFERRED EMBODIMENTS

Figure 1:
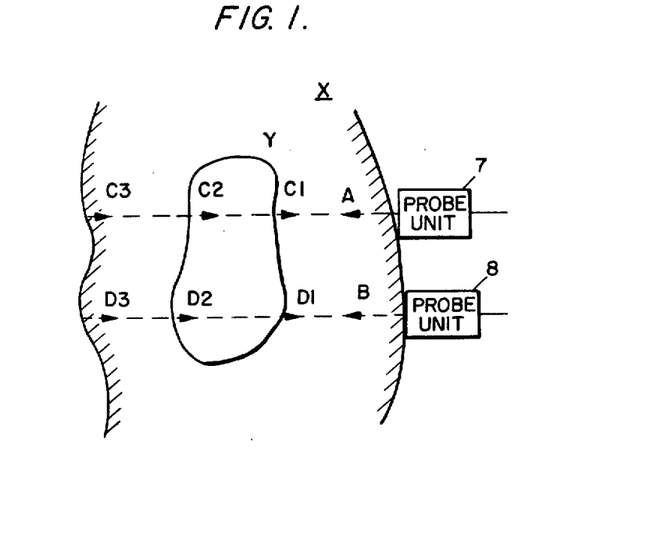
FIGS. 1 and 2 respectively show the principle of this invention.
Figure 2:
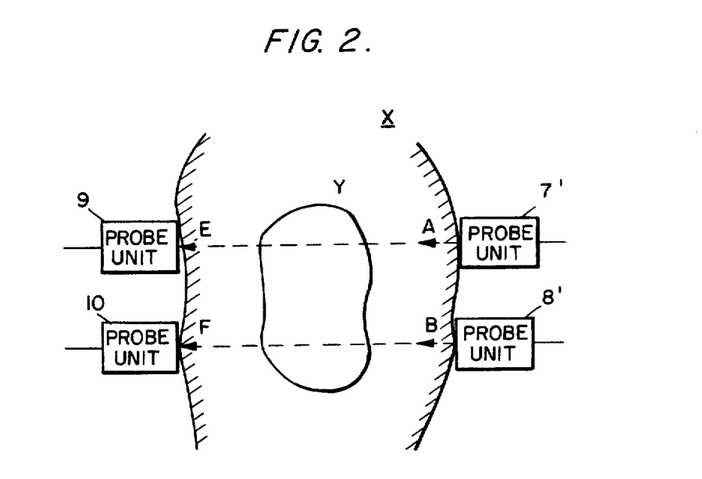

FIGS. 1 and 2 show the basic principle of this invention. FIG. 1 shows an example of the echo type system with probes 7, 8 containing an electric-acoustic transducer emitting almost simultaneously the ultrasonic waves A, B to a measured object. Here, two kinds of ultrasonic waves A, B respectively have different characteristics.

The ultrasonic wave A is partly reflected from the area of the object X where tissue changes. Namely, the echo waves C1 and C2 are returned from the boundary of the organ Y, and the echo wave C3 from the boundary of the object X. In the same way, the echo waves D1, D2, D3 are returned from the object X for the ultrasonic wave B.

These echo waves are received by the probes 7, 8 and then converted to electrical signals. However, the probes 7, 8 receive not only the echo waves of the ultrasonic waves emitted from one particular probe, but also the ultrasonic waves emitted from the other probe. In other words, the probes 7, 8 additionally receive echo waves D1 to D3, and C1 to C3, respectively, and convert them into electrical signals. For this reason probes 7 and 8 respectively isolate and extract the component of echo waves C1 to C3 and D1 to D3 from all the electrical signals received by each. The timed series of extracted echo waves is used as the tomographic information of location of the probes 7, 8.

In the case of the echo type system, the probes 7, 8 may be used for only generation and additional electric acoustic transducers may be used for reception instead of using probes 7, 8.

For the process of B-mode, a so-called mechanical linear scanning method where the probes 7, 8 are moved mechanically, or an electronic linear scanning method where a large number of probes 7, 8 are arranged in parallel in the form of an array and scanning is carried out electrically, may be employed. It is also possible to apply the sector scanning method which will be described later. The ultrasonic waves A, B are not required to be generated exactly at the same time. It is enough that ultrasonic wave B is generated before previously generated ultrasonic wave A reaches the maximum diagnostic depth.

FIG. 2 shows an example of the transmission type system, where two pairs of probe units 7', 9 and 8', 10 providing electric-acoustic conversion elements are arranged face-to-face respectively.

The probe units 7', 8' generate, respectively, the ultrasonic waves A, B to the object X. The ultrasonic waves A, B are two kinds of waves having different characteristics.

The transmission wave E obtained when the ultrasonic wave A transmits through the object X, including an organ Y, is received by the probe unit 9 and converted to an electrical signal. Similarly, the transmission wave F obtained when the ultrasonic wave B transmits through the object X, including an organ Y, is received by the probe unit 10 and converted to an electrical signal. The probe units 9, 10 receive both the transmission waves E and F, as in the case of the echo type system mentioned previously. Therefore, probe units 9 and 10 must isolate and extract the components of transmission waves E and F from all the electrical signals received by them.

In the case of a transmission type system, it is enough to use any of the probe units 9, 10 as the reception unit. By applying the mechanical or electronic linear scanning as in the case of the echo type system, the B-mode process can be employed. Also, sector scanning can be applied.

Then, ultrasonic waves having different characteristics used in this invention will be explained below.

(1) The frequency type system uses ultrasonic waves of different frequencies as the ultrasonic waves A, B:

FIG. 3 shows the waveforms of an embodiment of the frequency type system. In this figure, the generated wave and echo wave corresponding to FIG. 1 are indicated on the time axis t.

Figure 3A:
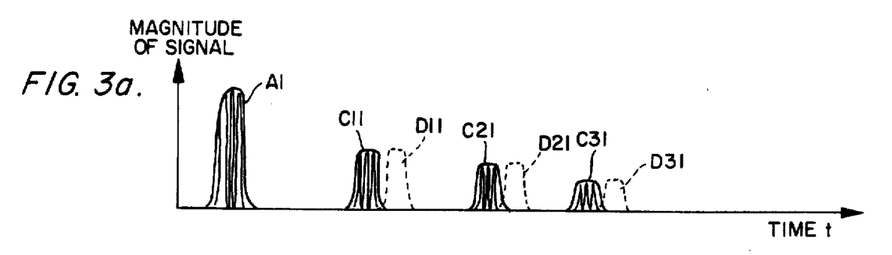
FIGS. 3a–3d show types of waveforms used in an embodiment of this invention.
Figure 3B:
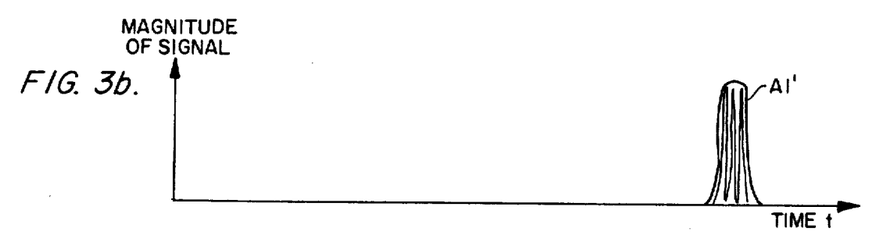
Figure 3C:
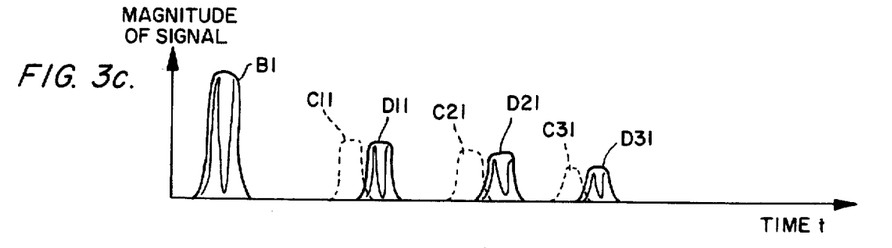
Figure 3D:
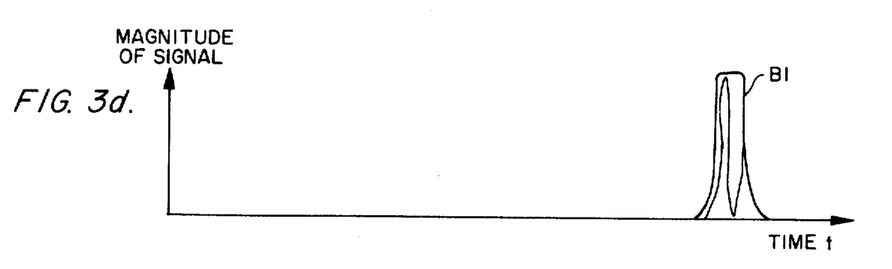

Namely, the probe 7 generates the ultrasonic wave A1 in frequency of 2 MHz shown in FIG. 3a, while the probe 8 generates the ultrasonic wave B1 in frequency of 1 MHz shown in FIG. 3c. The ultrasonic wave A1 causes the echo waves C11, C21, C31, while the ultrasonic wave B1 causes the echo waves D11, D21, D31. The received waves of the probe units 7, 8 are respectively the combined waves of each echo waves as shown in FIGS. 3a and 3c and these combined waves are converted into electrical signals. The elements of the received wave having the frequency corresponding to each ultrasonic wave are isolated and extracted from this electrical signal via the band pass filter for the frequency (1 MHz and 2 MHz) corresponding to each ultrasonic wave.

(2) The waveform type system uses ultrasonic wave of different waveforms for the ultrasonic waves A and B:

This waveform type is system classified into a one-waveform width type system and a two-waveform shape type system.

The waveforms of an embodiment of the waveform width type system is shown in FIG. 4, where the generated wave and the echo wave corresponding to those in FIG. 1 are indicated on the time axis t. The probe unit 7 receives the ultrasonic wave A2 having a width of T1 and frequency of 1 MHz shown in FIG. 4a, while the probe unit 8 generates the ultrasonic wave B2 having a width of T2 and frequency of 1 MHz shown in FIG. 4c. The ultrasonic wave A2 causes the echo waves C12, C22 and C32 having a width of T1, while the ultrasonic wave B2 causes the echo waves D12, D22, D32 having a width of T2. The signal received by both probe units 7, 8 is the combination of both echo waves as shown in FIGS. 4a and 4c, and these combined signals are converted to electrical signals. The element of the received signal having the width corresponding to that of each emitted ultrasonic wave are isolated and extracted from the received electrical signal via the wave form width isolation filter.

For the waveform shape type system, the gradients of waveforms having combined rectangular and sawtooth shapes are used.

FIG. 5 shows the waveforms of an embodiment of the waveform shape type system, wherein waveforms have different gradients, and where the generated wave and echo wave corresponding to those in FIG. 1 are indicated on the time axis t.

Figure 5A:
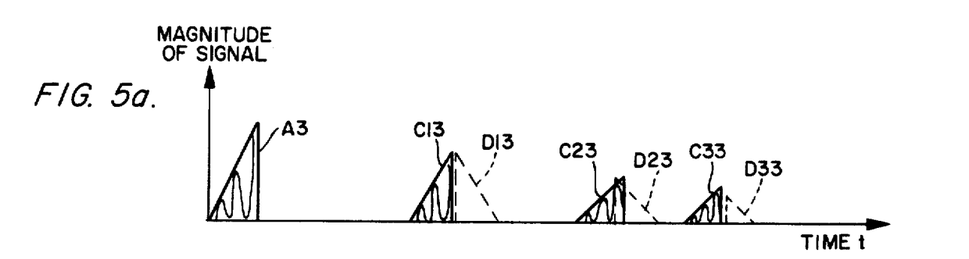
FIGS. 5a–5d show other types of waveforms used in an embodiment of this invention.
Figure 5B:
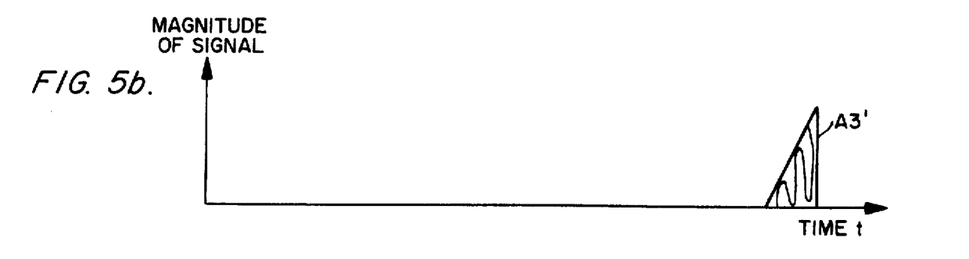
Figure 5C:
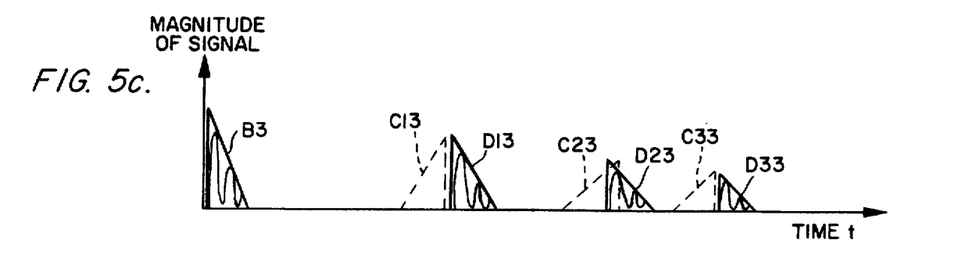
Figure 5D:
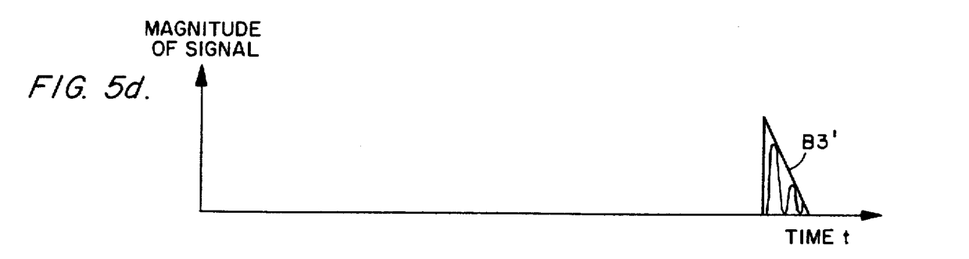

The probe unit 7 generates the sawtooth ultrasonic wave A3 having a positive gradient with a frequency of 1 MHz shown in FIG. 5a, while the probe unit 8 generates the sawtooth ultrasonic wave B3 having a negative gradient with a frequency of 1 MHz shown in FIG. 5c. The ultrasonic wave A3 causes the sawtooth echo waves C13, C23, C33 having the same positive gradient, while the ultrasonic wave B3 causes the sawtooth echo waves D13, D23, D33 having the same negative gradient. The signal received by both probe units 7 8 is the combination of both echo waves as shown in FIGS. 5a and 5c, and these combined waveforms are converted into electrical signals. The elements of the received signal having the gradient corresponding to that of each emitted ultrasonic wave is isolated and extracted from the received electrical signal via the waveform shape isolation filter.

(3) The pulse train type system uses ultrasonic waves of different pulse trains for the ultrasonic waves A and B:

FIG. 6 shows the waveforms of an embodiment of the pulse train type system, where the generated wave and echo wave corresponding to those in FIG. 1 are indicated on the time axis t.

Figure 6A:
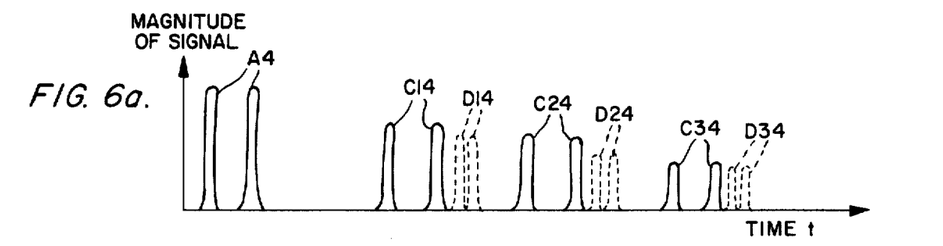
FIGS. 6a–6d show types of pulse trains used in an embodiment of this invention.
Figure 6B:
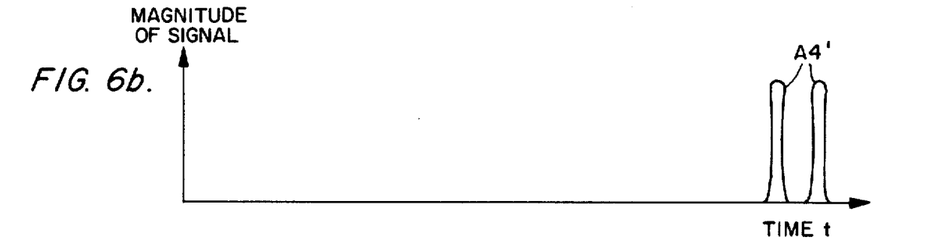
Figure 6C:
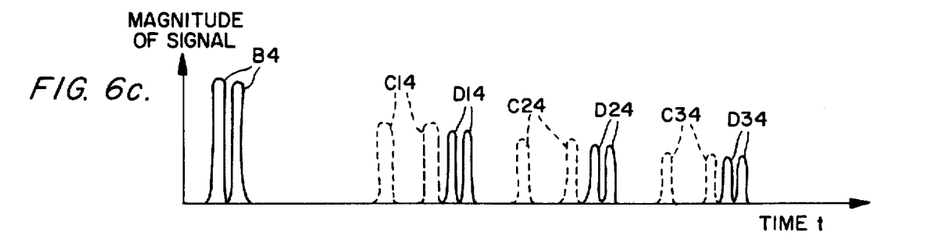
Figure 6D:
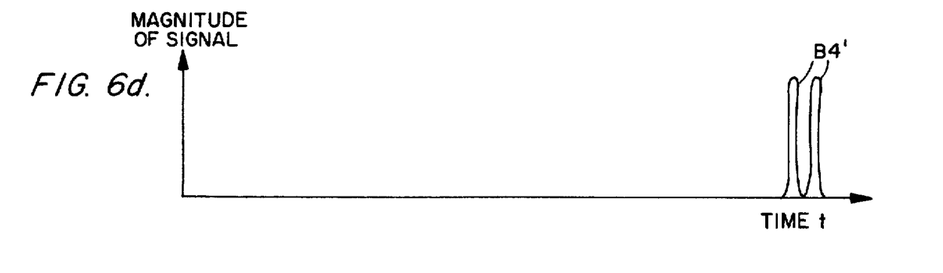

The probe unit 7 generates the ultrasonic wave pulse train A4 in the arrangement shown in FIG. 6a, while the probe unit 8 generates the ultrasonic wave pulse train B4 in the arrangement shown in FIG. 6 (c). The ultrasonic wave pulse train A4 causes the echo waves C14, C24, C34 in the same pulse train, while the ultrasonic wave pulse train B4 causes echo waves D14, D24, D34 in the same pulse train. The signals received by both probe units 7, 8 are combined waveforms of both echo wave pulse trains as shown in FIGS. 6a and 6e, and these pulse trains are converted to electrical signals. The received signal having the pulse train arrangement corresponding to that of each emitted arrangement of ultrasonic pulses is isolated and extracted from the received electrical signals via the pulse arrangement component extraction filter.

The pulse arrangement type system also is applicable to pulses having different pulse width and different pulse arrangement.

(4) A combination of any two types among types (1), (2) or, (3) mentioned above, or a combination of more types is also possible.

One embodiment of this invention is explained hereunder in details.

In an example explained below, the echo wave is used as the received wave, but it is also possible to use the transmission wave or diffraction wave as the received wave.

Figure 7:
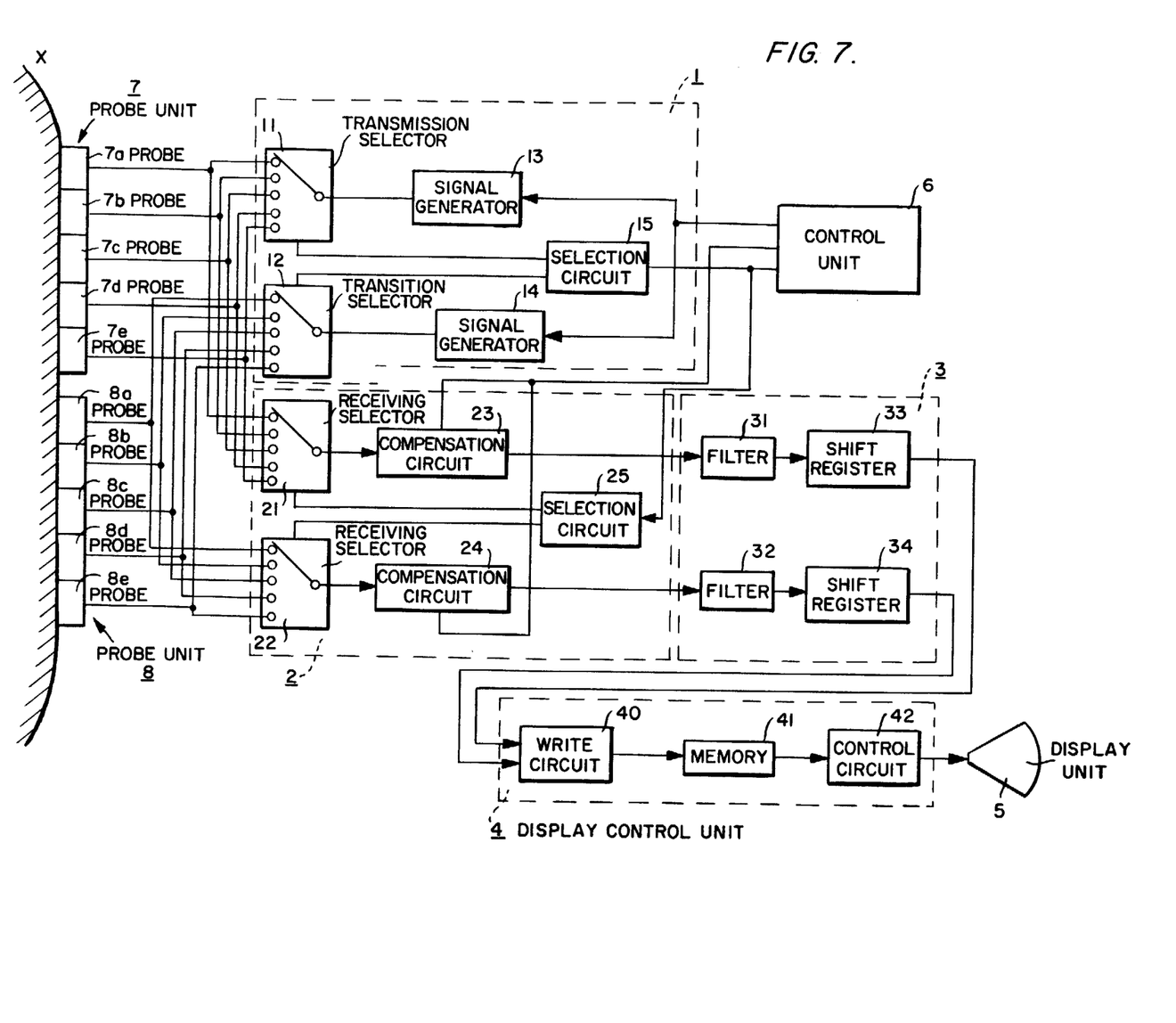
FIG. 7 shows a block diagram of an embodiment of this invention.

FIG. 7 shows a basic block diagram of an embodiment of this invention. In this figure, reference numeral 1 is the transmission unit; 2 is the receiving gate unit; 3 is the receiving processing unit; 4 is the display control unit; 5 is the display unit; and 6 is the control unit; 7 is the first probe unit; 8 is the second probe unit.

The first and second probe units 7, 8 are the array type electric-acoustic transducers of a well-known type respectively having five probes 7a, 7b, 7c, 7d, 7e, and 8a, 8b, 8c, 8d, 8e.

This array type electric-acoustic transducer is a piezoelectric element, which generates ultrasonic waves according to the given frequency signal and generates electrical signals according to the echo wave returning from the measured object X.

The transmission unit has the first and second transmission selectors 11 and 12. The first transmission selector 11 corresponds to the first probe unit 7, while the second transmission selector 12 corresponds to the second probe unit 8.

Each of the transmission selectors 11 and 12 has one input terminal and five output terminals, and each of five output terminals of the first transmission selector 11 is respectively connected to each probe 7a to 7e of the first probe unit 7. Each of five output terminals of the second transmission selector 12 is connected to each probe 8a to 8e of the second probe unit 8. The input terminals of both transmission selectors 11 and 12 are respectively connected to the first and second signal generator circuits 13 and 14. The input and output terminals of each of the transmission selectors 11 and 12 are connected by means of a rotating arm, which is capable of selectively and sequentially connecting output terminals in accordance with the command issued from the selection circuit 15.

The transmission selectors 11 and 12 are explained by the relation between the rotating arm and the contacts. It is recommended to use as an alternative a well-known electrical selection circuit having the structure of a gate circuit.

The selection circuit 15 connects and directs the switching of transmission selectors 11 and 12 in accordance with a command issued from the control unit 6. The first and second signal generator circuits 13 and 14 output the signals for generating ultrasonic waves A, B in accordance with a command issued from the control unit 6.

Transmission unit 1 outputs a signal for generating the ultrasonic wave A from the first signal generator circuit 13 and a signal for generating the ultrasonic wave B1 from the second signal generator circuit 14. Thus the signals are sent to the probes 7a to 7e and 8a to 8e by means of the probes being connected to the selection output terminals of transmission selectors 11 and 12, and thus through the rotating arm to the signal generators 13 and 14, in accordance with a command issued from the selection circuit 15.

In FIG. 7, the probes 7a and 8a are selected, and the ultrasonic wave A is generated from the probe 7a, while the ultrasonic wave B is emitted from the probe 8a.

Then, the transmission selectors 11 and 12 respectively select the second output terminals according to a command issued from the selection circuit 15, so the first and second signal generator circuits 13, 14 are respectively connected to the probe 7b, 8b. When a command is issued from the control unit 6, the output signals corresponding to said ultrasonic waves A, B are generated from the first and second signal generator circuits 13, 14. Thereby the ultrasonic waves A, B are transmitted from the probes 7b, 8b.

Thus, so-called electronic linear scanning is carried out.

The waveforms B, D in FIG. 3 to FIG. 6 respectively show the relation between emitted and reflected ultrasonic waves of probes 7b, 8b in each waveform, frequency and pulse train type systems.

Ultrasonic wave generation period from the probe 7a to 7b is exactly the same as that in the prior art.

The first and second signal generator circuits 13, 14 are oscillators generating different frequencies for the frequency type system, waveform generator circuits generating different waveforms for the waveform type system or the pulse train generating circuits generating different pulse trains for the pulse train type system. These circuits are already well-known and are not explained here in detail.

The echo waves resulting from ultrasonic waves transmitted from the transmission unit 1 as explained above are processed by the receiving gate units and receiving signal processing unit as described below.

The receiving gate unit 2 contains the first and second receiving selectors 21 and 22. The first receiving selector 21 corresponds to the first probe unit 7, while the second receiving selector 22 corresponds to the second probe unit 8.

Each of the receiving selectors 21 and 22 has one output terminal and five input terminals. Each of the five input terminals of the first receiving selector 21 is respectively connected to the probes 7a to 7e of the first probe unit 7. Each of five input terminals of the second receiving selector 22 is respectively connected to the probes 8a to 8e. The output terminals of receiving selectors 21, 22 are respectively connected to the first and second gain compensation circuits 23, 24. The rotating arms being connected with the input terminals of the receiving selectors 21 and 22 selectively and sequentially connect the input terminals in accordance with a command issued from the selection circuit 25. The receiving selectors 21 and 22 are explained by the relation between the rotating arm and contacts. It is recommended to use as an alternative a well-known electric selector circuit having the structure of a gate circuit.

The selection circuit 25 connects and directs the switching of receiving selectors 21 and 22 according to a command issued from the control unit 6.

The gain compensation circuits 23 and 24 are provided for compensating attenuation of the reflected waves by increasing the gain according to elapsed time since the reflected waves returning from the area deep in the measured object are attenuated. The gain compensation circuits 23 and 24 change respectively the above-mentioned gain according to elapsed time by means of a command which the control unit 6 sends after generating a command for output of ultrasonic waves.

Therefore, the receiving gate unit 2 connects the signals to the selected input terminals of the receiving selectors 21, 22 in accordance with a command issued from the selection circuit 25.

The electrical signals obtained from the echo waves coming from the probes 7a to 7e and 8a and 8e are input respectively to the gain compensation circuits 23, 24.

In FIG. 7, the probes 7a and 8a are selected and an electrical signal corresponding to the received echo wave sent from the probe 7a is input to the gain compensation circuit 23, while an electrical signal corresponding to the received echo wave sent from the probe 8a to the gain compensation circuit 24.

The receiving selectors 21 and 22 select sequentially the probes 7b and 8b, 7c and 8c, 7d and 8d, 7e and 8e corresponding to the selection process carried out by the transmission selectors 11 and 12, and thereby electronic scanning is carried out in synchronization with the selective operation of the transmission selector.

C11 to C31, C12 to C32, C13 to C33, C14 to C34, D11 to D31, D12 to D32, D13 to D33, D14 to D34 in FIG. 3 to FIG. 6 respectively show output electrical signals of the probes 7a to 8a in each type of system.

Outputs of the gain compensation circuits 23 and 24 are input to the receiving signal processing unit 3.

Figure 8:
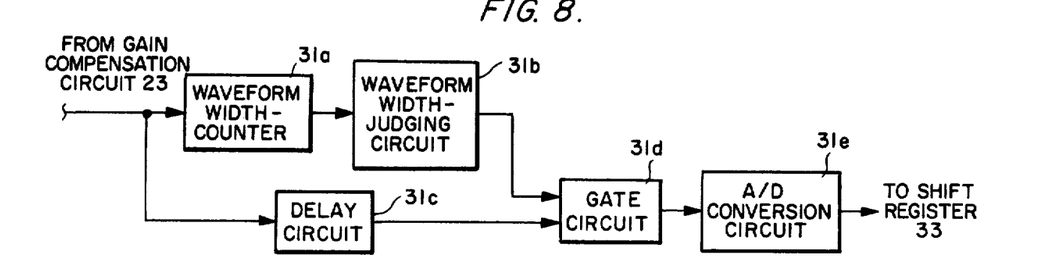
FIGS. 8, 9 and 10 show block diagrams of embodiments of the extraction filter of this invention.
Figure 9:
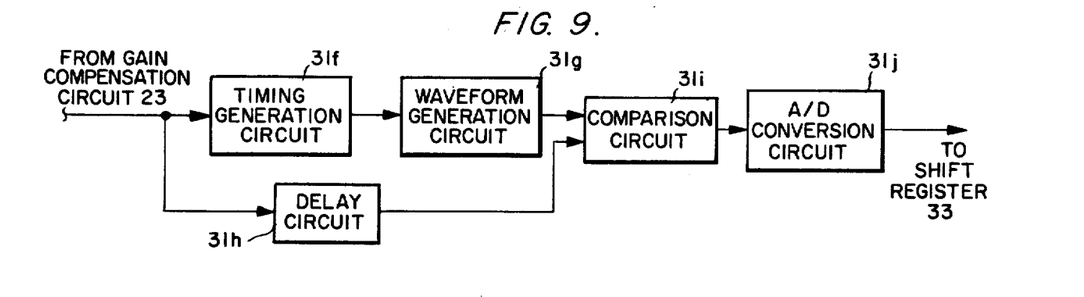
Figure 10:
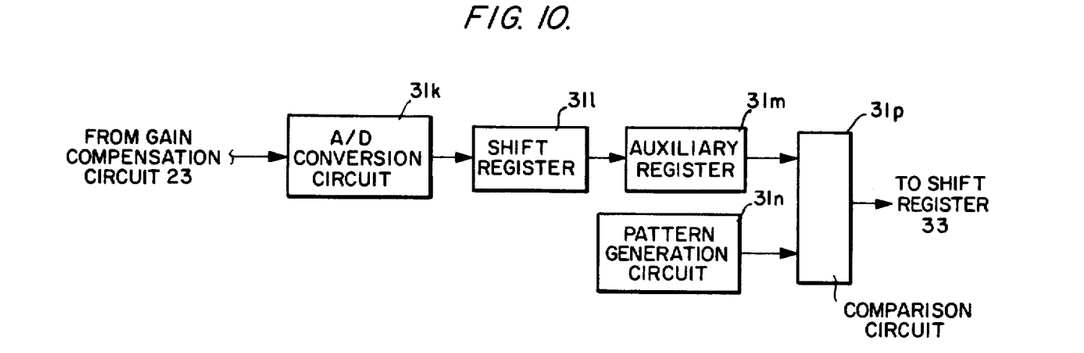

The receiving processing unit 3 comprises the first and second extraction filters 31, 32 and the first and second shift registers 33, 34. The first extraction filter 31 extracts only the echo wave components corresponding to the generated ultrasonic wave A and then sends them to the shift register 33 after analog-to-digital conversion. The second extraction filter 32 extracts only the echo waves corresponding to the generated ultrasonic wave B and sends them to the shift register 34 after analog-to-digital conversion. As the filter structure, the band pass filter of each generated ultrasonic wave is used for the frequency type system, while a filter shown in FIG. 8 and FIG. 9 is used for the waveform system and a filter shown in FIG. 10 is used for the pulse train type system.

Information thus stored in the shift registers 33, 34 are digital values of echo waves according to the time sequence of the emission of the ultrasonic waves. Digital values of this time series are input to display control unit 4 and displayed on the display unit 5.

The display control unit 4 has a frame memory 41, write circuit 40 and display control circuit 42. The write circuit 40 assigns the output signals of shift registers 33, 34 to the corresponding locations of the frame memory 41 in accordance with the locations of probes 7a to 7e, 8a to 8e. The display control circuit 42 sends the storage information from the frame memory 41 at the scanning timing of the display unit 5 and causes a tomographic image to appear on the display unit by displacing echo waves of each time series.

The ultrasonic waves A, B are thus generated, the echo waves are received and a tomographic image is displayed on the display unit by isolating and extracting electrical signals corresponding to said echo waves. An embodiment of a waveform extraction filter as shown in FIG. 8 is explained below.

In FIG. 8, reference numeral 31a is a waveform width counter; 31b is a waveform width judging circuit; 31c is a delay circuit; 31d is a gate circuit; 31e is an analog digital conversion circuit.

Figure 4A:
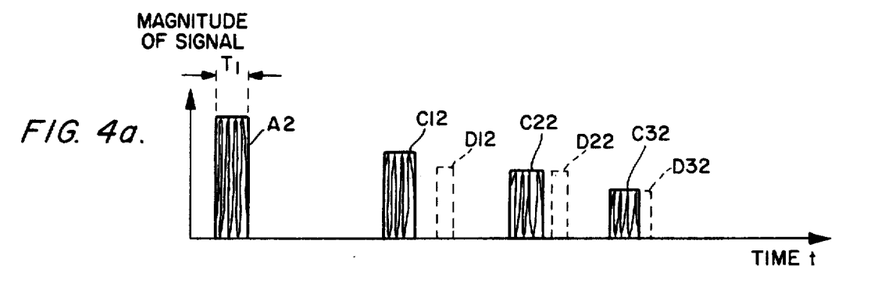
FIGS. 4a–4d show other types of waveforms used in an embodiment of this invention.
Figure 4B:
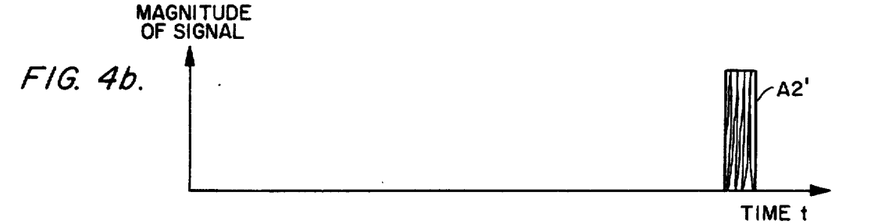
Figure 4C:
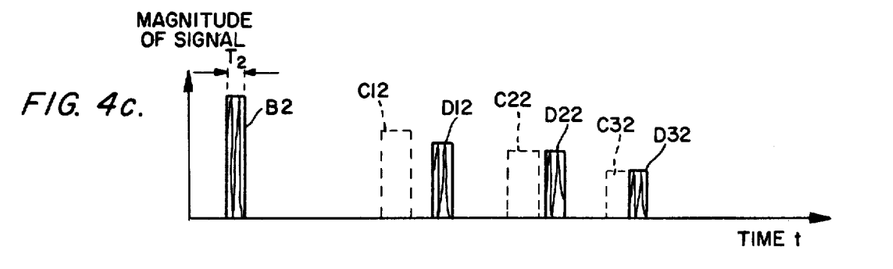
Figure 4D:
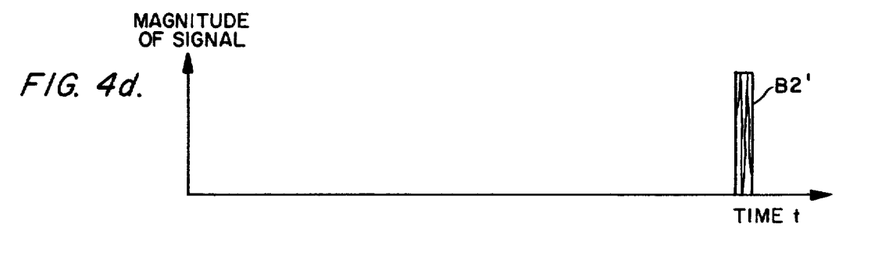

The operation of extraction filter 31 is as follows. An output signal of the gain compensation circuit 23 is input to the waveform width counter 31a, where the waveform width is counted. For example, in the case of FIG. 4 (a), the waveform width counter 31a counts the waveform width of the combined signal of gain-compensated echo waves of C12, D12, C22, D22, and C32 and then outputs it. The waveform width judging circuit 31b selects the width T1 from counted values and generates a gate signal. Namely, it sends the gate signal of the width T1 for the signal C12, and a gate signal of the width T1 for the signal C22. The combined signal of C32 and D32 has the width of T1 or more and therefore the gate signal of the with T1 is also sent. Since an output signal of the gain compensation circuit 23 is delayed by the delay circuit 31c and then input to the analog gate circuit 31d, only the signals C12, C22, C32 are output from the analog gate circuit 31d. An output of the analog gate circuit 31d is sampled by the analog digital conversion circuit 31e as an adequate sampling interval, then analog-to-digital conversion takes place and the signal is sent to the shift register 33. In the same way, the waveform width extraction filter 32 has similar structure and carries out the same operation, except for the only difference being that the waveform width judging circuit 31b selects the width T2 and sends the gate signal of the width T2, and the gate signal of the width T2 is sent for the waveforms having the width of T2 or more.

FIG. 9 shows a block diagram of a waveform shape extraction filter which is used as the waveform extraction filter for extracting the waveform shown in FIG. 5. In this figure, reference numeral 31f is a timing generation circuit; 31g is a basic waveform generation circuit; 31h is a delay circuit; 31i is a comparator circuit; and 31j is an analog digital conversion circuit.

Operation of this circuit will be explained below. An output signal of the gain compensation circuit 23 is sent to the timing generation circuit 31f. The timing generation circuit 31f detects that a signal is greater than zero and generates an output pulse in time with the detected signal. This output pulse is sent to the basic waveform generation circuit 31g, and thereby the waveform A3, which is the same as the generated ultrasonic wave, is generated in time with the output pulse. This basic waveform is sent to the comparison circuit 31i.

An output signal of the gain compensation circuit 23 being delayed by the delay circuit 31h is input to the comparison circuit 31i. Therefore, the comparison circuit 31i extracts a waveform which is the same as the basic waveform from the output of delay circuit 31h, namely the signals C13, C23, C33 shown in FIG. 5 (a), and then sends them to the analog digital conversion circuit 31j. The analog digital conversion circuit 31j samples them at an adequate sampling interval and sends them to the shift register 33 after analog-to-digital conversion.

Similarly, the waveform shape extraction filter 32 employs the same structure and, the only difference is that the signal B3 shown in FIG. 5 (c) is generated as the basic waveform.

FIG. 10 shows a block diagram of the pulse train extraction filter, which extracts the pulse train shown in FIG. 6. In this figure reference numeral, 31k is an analog digital conversion circuit; 31l is a shift register; 31m is an auxiliary register; 31n is a basic pattern generation circuit; and 31p is a comparison circuit.

Operation of this filter will be explained below. An output signal of the gain compensation circuit 23 is converted to a digital value by the analog digital conversion circuit 31k. The converted digital values are sequentially stored in the shift register 31l. The storage data of the shift register 31l is then sent sequentially to the auxiliary register 31m.

For example, when the basic pattern indicates a signal A4 of 10 bits as shown in FIG. 6 (a), the auxiliary register 31m also registers a signal of 10 bits. The 10-bit data of the auxiliary register 31m is compared with the 10 bits basic pattern of the basic pattern generation circuit 31n by the comparison circuit 31p each time the 1-bit data is sent from the shift register 31l, and a result of comparison is sent to the shift register 33.

Similarly, the pulse train extraction filter 32 has the same structure, except for the only difference being that the basic pattern is the 10-bit pattern of B4 shown in FIG. 6 (c).

In an embodiment of the abovementioned electronic linear scanning, the probes 7 8 are constructed to move freely. Therefore, it is possible in the examples shown in FIGS. 1, 2 and 7 to clearly reproduce the boundary of an organ Y by placing the probes 7 8 at different angles from organ Y and irradiating ultrasonic waves from different angles to said organ Y.

On the occasion of combining and displaying an acoustic image based on the generated ultrasonic waves from both probes by constructing probes 7, 8 for free movement, a highly accurate combined display becomes possible. To achieve this it is also necessary to make use of the probe location detection mechanism used for an embodiment of the electronic scanning system.

Then, an example of the electronic sector scanning system will be explained.

Both electronic scanning systems are used as sector scanning systems and mechanical scanning system are known. In the electronic scanning system, plural electric-acoustic transducers are arranged in parallel in the form of an array and are so constructed that the ultrasonic waves can be generated at the desired angle selected freely and moreover, the focusing can be set in such the desired direction by changing the generation timing of the adjacent electric-acoustic transducers. In the case of the mechanical scanning system, the electric-acoustic transducers are so constructed that the ultrasonic waves can be generated in the desired angle selected freely by rotating the electric-acoustic transducers in the form of the sector around the rotating axis. The sector scanning system is particularly convenient for diagnosis of such areas as the heart.

Figure 11:
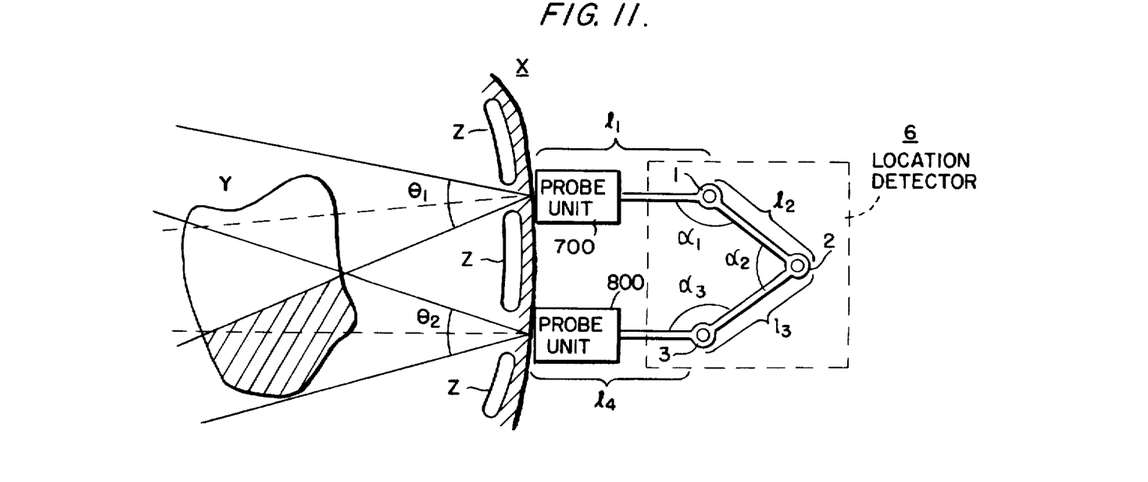
FIG. 11 shows another embodiment of this invention.

FIG. 11 shows an embodiment indicating the principle of the ultrasonic diagnostic system with an electronic sector scanning system using echo pulses (reflected waves) of ultrasonic waves. In this figure, 700, 800 are respectively, the first electronic sector scanning probe and the second electronic sector scanning probe.

In the existing types of electronic sector scanning systems, the first electronic sector scanning type probe 700 is used solely. Generation and reception are sequentially repeated by changing the generation angle bit-by-bit. Thus, it is difficult to display a total image of the heart Y within the object X.

In the present invention, the second electronic sector scanning type probe 800 is used in addition to the first electronic sector scanning type probe 700, and thereby a part of the heart which cannot be displayed by the first electronic sector scanning type probe 700 alone (indicated as the hatched area) can be displayed successfully.

It is recommended to employ the multi-beam system using ultrasonic waves having different characteristics for the first and second electronic sector scanning type probes 700, 800 can be employed for simultaneous scanning by both probes. Ultrasonic waves having different frequencies or different waveforms may be used.

An an example, toward the uppermost angle shown in the FIG. 11, an ultrasonic wave of 2 MHz is generated from the first electronic sector scanning type probe 700, while toward the lowermost angle an ultrasonic wave of 3 MHz is generated from the second electronic sector scanning type probe 800. In this case the generation timing of these ultrasonic waves is the same in order to obtain a display of a moving object like the heart without any flickering.

As a result, in the case of this embodiment, the echo wave due to mismatching of acoustic impedance of organs inside the measured object X is received mainly from the heart Y by the first electronic sector scanning type probe 700 and the second electronic scanning type probe 800. The first electronic sector scanning type probe 700 also receives the ultrasonic wave signal of 3 MHz generated from the second electronic sector scanning type probe 800 in addition to receiving the ultrasonic wave signal of 2 MHz generated by said first electronic sector scanning type probe alone. Therefore, the 2 MHz signal is isolated and extracted using the 2 MHz band-pass filter and thus the picture information of the uppermost angle can be obtained.

Then, a transmitting angle of each probe is minutely shifted to the lower angle direction in FIG. 11 and similar processing is carried out. By repeating such processing for angles of $\theta_1$, $\theta_2$, the picture information in the range of angle $\theta_1$ can be obtained from the first electronic sector scanning type probe 700, while the picture information in the range of angle $\theta_2$ can be obtained from the second electronic sector scanning type probe 800.

In FIG. 11, 6 is a location detector, for example a well-known resolver, which detects relative location by mechanically connecting the first electronic sector scanning type probe 700 and the second electronic sector scanning type probe 800 in order to determine the relative locations of the probes. 1, 2, 3 are rotating angle converters, which can freely set the optimum angle for diagnosis, and can provide for angles $\alpha_1$, $\alpha_2$ and $\alpha_3$, to be expressed as electrical signals respectively. For sufficient diagnostic measurement, it is necessary, first of all, to set the first electronic sector scanning type probe 700 and the second electronic sector scanning type probe 800 to the optimum location. Then the relative location information can be obtained from angular signals corresponding to angles $\alpha_1$, $\alpha_2$, $\alpha_3$ obtained from each rotating angle converter and the fixed rod length $l_1$, $l_2$, $l_3$, $l_4$. Namely, the contact points and center directions of the electronic sector scanning type probes 700, 800 and the measured object (specimen) X are determined.

The picture data obtained by said first electronic sector scanning type probe 700 and second electronic sector scanning type probe 800 are location-converted using the relative location information obtained from location detector 6 and then combined. Thereby, the picture of total areas covering the angles $\theta_1$ and $\theta_2$ can be displayed.

Figure 12:
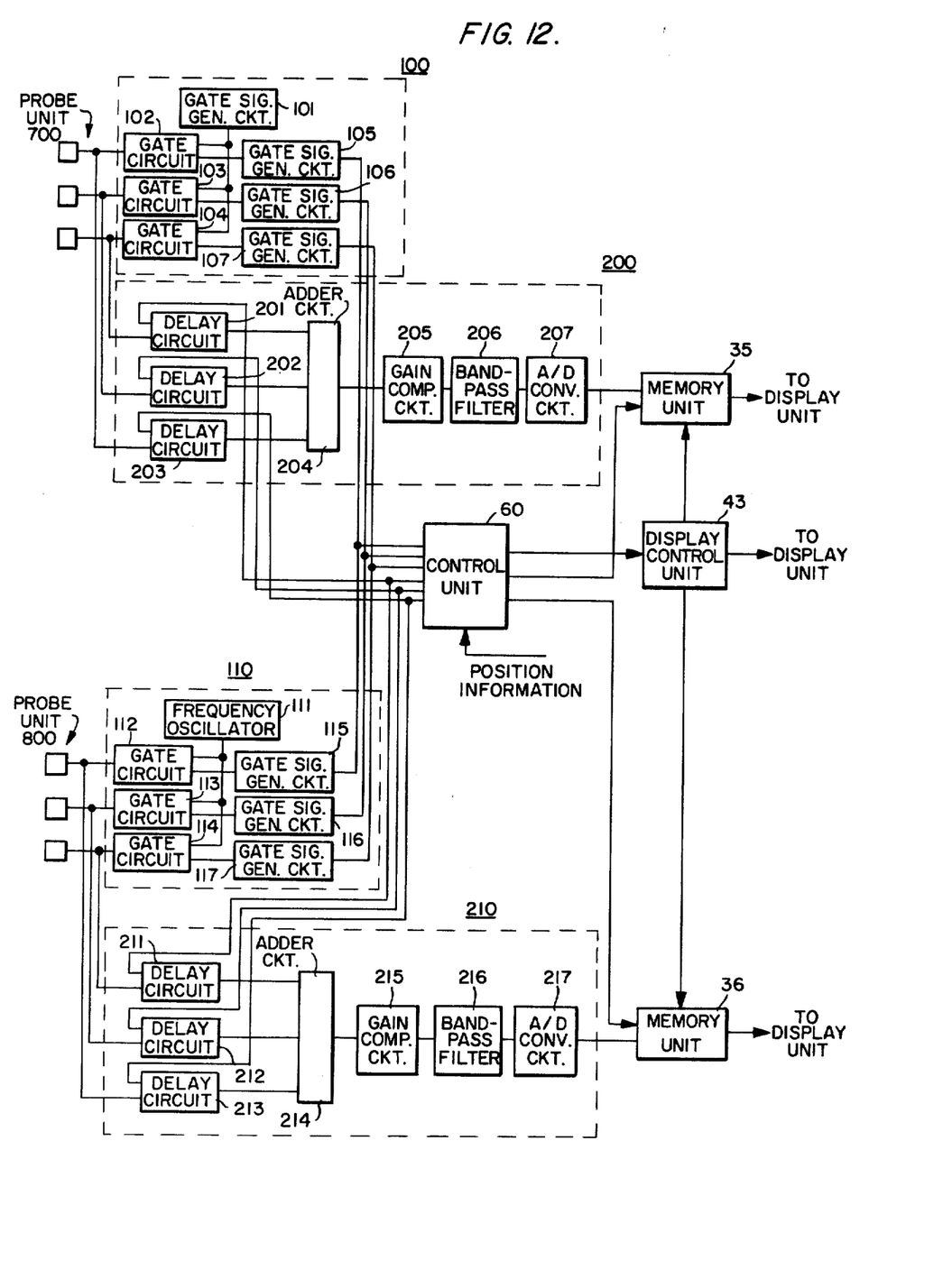
FIG. 12 shows a block diagram of another embodiment of this invention.

FIG. 12 shows a block diagram of a further embodiment of this invention. In this figure, the electronic sector scanning system is employed and it is applied to the echo wave type system. In this figure, 700, 800 are respectively the first and second electronic sector scanning type probes; 100, 110 are respectively the first and second transmission units; 200, 210 are respectively the first and second receiving units; 60 is a control unit; 35, 36 are respectively the first and second memory units; and 43 is a display control unit. The electronic sector scanning type probes 700, 800 are composed of at least three electric-acoustic transducers. The transmission units 100, 110 respectively have the frequency oscillators 101, 111. In a multi-beam system, the frequency of each oscillator 101 and 111 is different. For example, the oscillator 101 generates a frequency of 2 MHz, while the oscillator 111 oscillates a frequency of 3 MHz. The control unit 60 gives the signal generation command to each of the gate signal generating circuits 105, 106, 107, 115, 116 and 117. The gate signals of the gate signal generating circuits 105, 106, 107, 115, 116 and 117 respectively open the connected gate circuits 102, 103, 104, 112, 113 and 114; and thereby a signal from the oscillator 101 is transmitted to the electronic sector scanning type probe 700 consisting of three elements. A frequency signal from the oscillator 111 is transmitted to the electronic sector scanning type probe 800 consisting of three elements. Thereby the corresponding ultrasonic waves are generated from electronic sector scanning type probes 700, 800.

For the electronic sector scanning, it is necessary to generate the gate signals from the gate signal generating circuits 105, 106 and 107 at different times. When gate signals are generated sequentially from the gate signal generating circuits 105, 106 and 107, the direction of the ultrasonic wave emitted by electronic sector scanning type probe 700 advances to the lower left direction of FIG. 11. When these signals are generated in the reverse sequence, the direction of the ultrasonic wave emitted by ultrasonic sector scanning type probe 700 advances to the upper left direction of FIG. 11. Therefore, the ultrasonic wave is generated from the electronic sector scanning type probe 700 so as to scan a sector composed of the arcuate sections made by multiple emission angles by means of changing the gate signal generation timing.

The gate signal generating circuits 115, 116 and 117 also cause the electronic sector scanning type probe 800 to generate the ultrasonic waves in order to scan in the form of a sector. The ultrasonic wave of 2 MHz is thus generated from the electronic sector scanning type probe 700, while the ultrasonic wave of 3 MHz from the electronic sector scanning type probe 800 sequentially in accordance with the sector scanning. The reflected waves caused by these emitted ultrasonic waves returning from the measuring objective X are respectively received by the electronic sector scanning type probes 700 and 800, converted to electrical signals and then input to the receiving units 200, 210, respectively. The receiving units 200, 210 respectively have the delay circuits 201, 200 and 203 and 211, 200 and 213. Each of the delay circuits 201, 202, 203 and 211, 212, 213 is operated by the timing signal of the control unit 60. The control unit 60 gives the timing signals to the delay circuits 201, 202, 203 in the same transmission sequence and the transmission gate signals. Control unit 60 also gives the timing signals the delay circuits 211, 212, 213 in the same way. The electrical signals converted from the reflected waves, having passed the delay circuits 201, 202, 203, are combined in the adder circuit 204 and then output. Similarly, the signals having passed the delay circuits 211, 212, 213 are combined in the adder circuit 214 and then output. Outputs of the adder circuits 204, 214 are input to the gain compensation circuits 205, 215, respectively. The gain compensation circuits 205, 215 change the gain according to elapsed time to compensate for attenuation because the reflected waves returning from areas deep in object X are severely attenuated. Usually a logarithmic amplifier is used for this kind of gain compensation circuit. The signals thus gain-compensated are input to the band-pass-filters 206, 216. The band-pass filter 206 allows the 2 MHz signals of the oscillator 101 to pass, while the band-pass filter 216 allows the 3 MHz signals of oscillator 111 to pass.

Therefore, the band-pass filter 206 outputs only the reflected wave component corrresponding to the 2 MHz generated ultrasonic wave of the electronic sector scanning type probe 700, while the band-pass filter outputs 216 only the reflected wave component corresponding to the 3 MHz generated ultrasonic wave of the electronic sector scanning type probe 800.

These outputs are input to the analog digital conversion circuits 207, 217, respectively, then converted to the digital values at the specified sampling rate and input to the memory units 35, 36 as the picture information.

The address signals corresponding to the sector angles are input to the memory units 35, 36 from the control unit 60. Thus, the digitalized picture information is stored in the addresses corresponding to the sector scanning angles of the memory units 35, 36.

On the other hand, the display control unit 43 receives the coordinates of origin of the display screen and sector scanning directions (direction indicated by the dotted line at the centers of angles $\theta_1$, $\theta_2$ in FIG. 11) of the first and second electronic sector scanning type probes 700, 800. This data is on the location information derived from location detector 6 (in FIG. 11) and routed through control unit 60.

Then, the control unit 60 sends a "display start" command to the display control unit 43. In accordance with such "display start" command, the display control unit 43 sequentially sends the electron beam deflection signal according to the sector scanning angle to the display unit using the CRT (not illustrated) and simultaneously sends the synchronization signal calling for the digitalized picture information corresponding thereto to the memory unit 35 or 36.

The memory unit 35 or 36 which has received such synchronization signal sequentially sends the digitalized picture information being stored in the address corresponding to the scanning location to the display unit.

The display unit displays a total picture of the heart Y of FIG. 11 on the CRT display screen using the deflection signal thus received for controlling the deflection and scanning of the electron beam, and using the digitalized picture information for intensity modulation synchronized to the deflection signal.

In this case, the timing of the picture information storage in the memory units 33, 34 and the display timing, are not always required to be synchronized.

In the above explanation, the electron beam of the CRT is used for sector scanning, but it is also possible to synchronize the sector scanning to an ordinary television raster by converting the coordinates of the digital data held by the memory units 33 and 34. In addition, the electronic sector scanning type probes 700, 800 are used in common for both transmission and reception, but it is possible to separately provide an electronic sector scanning type probe for reception only.

Figure 13A:
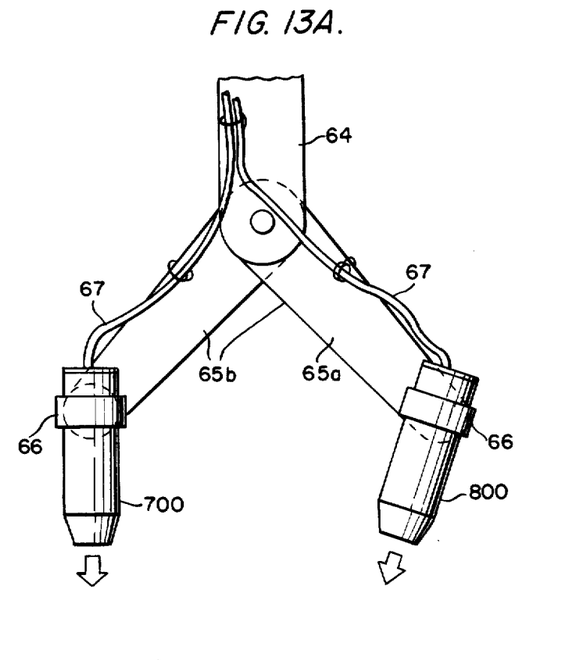
FIGS. 13A and 13B show construction of probe used in the embodiment of FIG. 11.
Figure 13B:
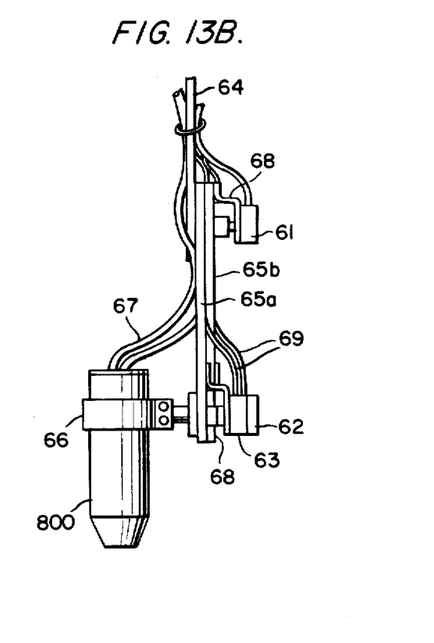

FIG. 13 shows the construction of the electronic sector scanning type probe used in FIG. 11. FIG. 13A shows the front view, while FIG. 13B shows a side view of it.

A first arm 65a is engaged with a support arm 64 without freedom of movement, while a second arm 65b is engaged with arm 64 and has freedom of rotation.

The rotation angle detector 61 being composed of a potentiometer and generates an output corresponding to a rotation angle of the arm 65b.

The probe 800 is engaged with the end of the arm 65a and has freedom of rotation by means of a metallic probe support 66. A rotation angle detector 62 is composed of a potentiometer and generates an output corresponding to the rotation of the probe 800. In the same way, the probe 700 is engaged with the end of the arm 65b and has freedom of rotation by means of the metallic probe support 66. A rotation angle detector 63 is composed of a potentiometer and generates an output corresponding to the rotation of the probe 700.

Reference numeral 68 identifies a settling metal, and 67, 69 are connecting cables.

Figure 14A:
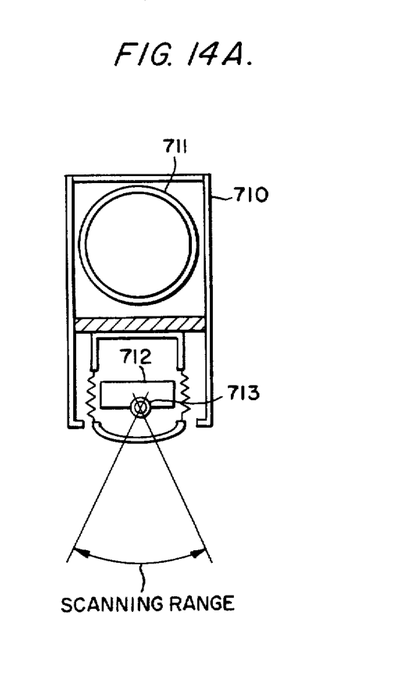
FIGS. 14A and 14B show another construction of the probe of FIG. 13.
Figure 14B:
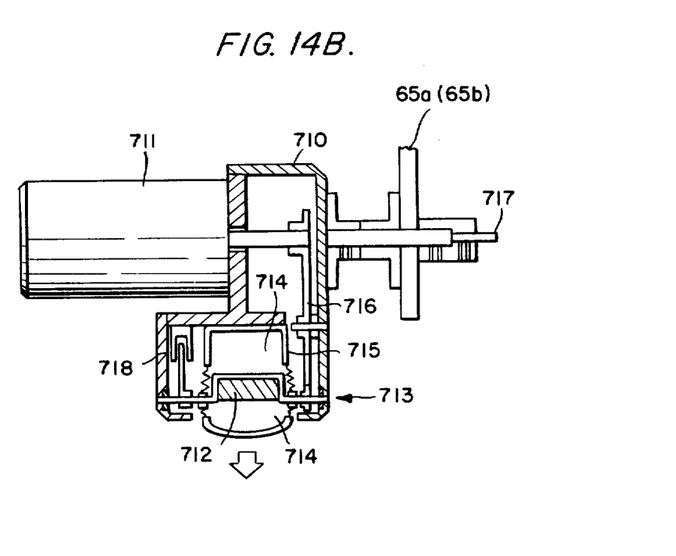

FIG. 14 shows a structure of the mechanical sector scanning type probe. FIG. 14A is a section of the front view, while FIG. 14B is a section of the side view. In this figure, probe 710 corresponds to probes 700, 800 shown in FIG. 13.

An electric-acoustic transducer 712 is accommodated within the variable capacitance type vessel 715 and is so constructed that it can rotate around axis 713. In the vessel 715, the matching liquid 714 for impedance matching is sealed.

The rotational force of a drive motor 711 is transmitted to an axis 713 via the gear 716. Therefore, a transducer 712 is rotated around the axis 713 by drive motor 711. This rotation is detected by the encoder 718. The probe 710 is coupled to the arm 65b which has freedom of rotation. This rotation is transmitted via axis 717 to rotating angle detector 62 composed of a potentiometer.

As explained above, this invention has realized elimination of noise due to interference by ultrasonic waves, even when plural kinds of ultrasonic waves are generated simultaneously from plural probes.

Moreover, according to this invention, a highly accurate combined display can be realized by detecting the location of the plural probes.

We claim:

1. An ultrasonic diagnostic system for obtaining an acoustic image of a measured object comprising:
   (a) a plurality of probe units being separated mutually, each probe unit being selectively and separately positionable in any direction and having an electric-acoustic transducer for both transmitting said ultrasonic waves and receiving said acoustic echo waves;
   (b) a transmitting circuit for causing said probe units to transmit ultrasonic waves having different characteristics almost simultaneously; and
   (c) a receiving circuit containing filters for isolating and extracting signals received from said transducers, said signals having properties respectively corresponding to acoustic echo waves resulting from said transmitted ultrasonic waves; whereby said system obtains the acoustic image of the measured object corresponding to a plurality of scanning lines formed by scanning of each of said probe units.

2. An ultrasonic system for obtaining an acoustic image of a measured object comprising:
   (a) a plurality of probe units, each probe unit being selectively and separately positionable in any direction and having an electric-acoustic transducer for both transmitting said ultrasonic waves and receiving said acoustic echo waves;
   (b) a transmitting circuit for causing said probe units to transmit ultrasonic waves having different characteristics almost simultaneously;
   (c) a receiving circuit containing filters for isolating and extracting signals received from said transducers, said signals having properties respectively corresponding to acoustic echo waves resulting from said transmitted ultrasonic waves; and
   (d) detecting mechanisms for detecting mutual locations of said probe units; whereby said system realizes an acoustic image of the measured object formed by output signals of said receiving circuit in accordance with the detected locations of said probe units.

3. An ultrasonic diagnostic system as claimed in claim 2, further comprising a coupling mechanism for mechanically and mutually coupling said probe units.

4. An ultrasonic diagnostic system as claimed in claim 1, 2 or 3, wherein each said probe unit comprises a plurality of said electric-acoustic transducers.

5. An ultrasonic diagnostic system as claimed in claim 1, 2 or 3, wherein at least a first and second ultrasonic wave are emitted in sequence so that said second ultrasonic wave is emitted before said first ultrasonic wave is reflected from said measured object.

6. An ultrasonic diagnostic system as claimed in claim 1, 2 or 3, wherein said different characteristics of the ultrasonic waves comprise differences in frequency of said ultrasonic waves transmitted from each said probe unit.

7. An ultrasonic diagnostic system as claimed in claim 1, 2 or 3, wherein said different characteristics of the ultrasonic waves comprise differences in the width of said ultrasonic waves of each said probe unit.

8. An ultrasonic diagnostic system as claimed in claim 1, 2 or 3, wherein said different characteristics of the ultrasonic waves comprise differences in the shape of the ultrasonic waves of each said probe unit.

9. An ultrasonic diagnostic system as claimed in claim 1, 2 or 3, wherein the ultrasonic waves of each said probe unit are in the shape of a sawtooth having a specific gradient, said different characteristics between the ultrasonic waves of each said probe unit being in the specific gradient of the ultrasonic waves of each said probe unit.

10. An ultrasonic diagnostic system as claimed in claim 1, 2 or 3, wherein the ultrasonic waves are emitted in a series of pulses comprising a pulse train, said different characteristics being each spacing between said pulses for the pulse trains of each said probe unit.

11. An ultrasonic diagnostic system as claimed in claim 10, wherein said different characteristics also comprise frequency, wave width, wave shape and wave gradient.

12. An ultrasonic diagnostic system as claimed in claim 3 further comprising a first detecting mechanism for detecting mutual angles of emission for said probe units, said first detecting mechanism being of the electronic type.

13. An ultrasonic diagnostic system as claimed in claim 3 further comprising a second detecting mechanism for detecting the angle of said probe unit to said measured object, said second detecting mechanism being of the electronic type.

14. An ultrasonic diagnostic system as claimed in claim 3, further comprising a first detecting mechanism for detecting mutual angles of emission for said probe units, said first detecting mechanism being of the mechanical type.

15. An ultrasonic diagnostic system as claimed in claim 3, further comprising a second detecting mechanism for detecting the angle of said probe unit to said measured object, said second detecting mechanism being of the mechanical type.

16. An ultrasonic diagnostic system as claimed in claim 2, wherein said transmitting circuit comprises: a first transmission selector, a second transmission selector, a selection circuit for controlling the switching of said first transmission selector and said second transmission selector, a first signal generator circuit, and a second signal generator circuit; and wherein said receiving circuit comprises a receiving gate unit and a receiving processing unit, said receiving gate unit comprising a first receiving selector, a second receiving selector, first and second gain compensation circuits for compensating attenuation of said signals from said transducers by increasing the gain of said signals from said transducers according to elapsed time, and a selection circuit for controlling the switching of said first receiving selector and said second receiving selector, and wherein said receiving processing unit comprises first and second extraction filters for transmitting particular electrical signal characteristics, and first and second shift registers for storing digital information corresponding to values associated with said echo wave signals according to the time sequence of the emission of each of said ultrasonic waves from said probe units.

17. An ultrasonic diagnostic system as claimed in claim 2 or 16 further comprising control means for sequencing information stored by said receiving circuit according to the detected location of each said probe unit.

18. An ultrasonic diagnostic system as claimed in claim 2 or 16 further comprising control means for sequencing information stored by said receiving circuit according to the detected location of each said probe unit and display means for displaying information stored in said receiving circuit according to the angle of each said probe unit to said measured object, as sequenced by said control means.

19. An ultrasonic diagnostic system as claimed in claim 2 or 16 further comprising control means for sequencing information stored by said receiving circuit according to the detected location of each said probe unit and display means for displaying information stored in said receiving circuit according to the mutual angle between said probe units, as sequenced by said control means.

20. An ultrasonic diagnostic system as claimed in claim 1, 2 or 3, wherein said electric-acoustic transducers are piezoelectric devices.

* * * * *